United States Patent
NaPier (10) Patent No.: US 8,104,467 B2
(45) Date of Patent: Jan. 31, 2012

(54) RAPID OROTRACHEAL INTUBATION GUIDE

(75) Inventor: Bradford Lee NaPier, Honolulu, HI (US)

(73) Assignee: Hanu Surgical Devices LLC, Honolulu, HI (US)

(*) Notice: Subject to any disclaimer, the term of this patent is extended or adjusted under 35 U.S.C. 154(b) by 987 days.

(21) Appl. No.: 12/051,793

(22) Filed: Mar. 19, 2008

(65) Prior Publication Data
US 2008/0230055 A1    Sep. 25, 2008

Related U.S. Application Data

(60) Provisional application No. 60/895,701, filed on Mar. 19, 2007.

(51) Int. Cl.
*A61M 16/00* (2006.01)
*A62B 9/06* (2006.01)
*A61C 5/14* (2006.01)

(52) U.S. Cl. ............... 128/200.26; 128/861; 128/207.14

(58) Field of Classification Search ............ 128/200.24, 128/200.26, 204.18, 207.14–207.17, 859, 128/860–863
See application file for complete search history.

(56) References Cited

U.S. PATENT DOCUMENTS

| | | | | |
|---|---|---|---|---|
| 4,112,936 A * | 9/1978 | Blachly | ........................ | 128/861 |
| 4,270,531 A * | 6/1981 | Blachly et al. | ........... | 128/207.14 |
| 4,495,945 A * | 1/1985 | Liegner | .................... | 128/200.26 |
| 5,386,821 A * | 2/1995 | Poterack | .................. | 128/200.26 |
| 5,626,128 A * | 5/1997 | Bradley et al. | ........... | 128/200.26 |
| 5,638,811 A * | 6/1997 | David | ....................... | 128/207.14 |
| 5,941,246 A * | 8/1999 | Roopchand | ............. | 128/207.14 |
| 6,086,529 A * | 7/2000 | Arndt | ............................. | 600/114 |
| 6,675,808 B2 * | 1/2004 | Karasic | ......................... | 128/859 |
| 2005/0252514 A1 * | 11/2005 | Taljaard | ................... | 128/207.14 |

FOREIGN PATENT DOCUMENTS
WO  PCT/US2008/057556    9/2008
* cited by examiner

*Primary Examiner* — Justine Yu
*Assistant Examiner* — Valerie L Skorupa
(74) *Attorney, Agent, or Firm* — Paradise Patent Services, Inc.; George E. Darby (57) ABSTRACT

A rapid orotracheal intubation guide device is disclosed that facilitates orotracheal intubation or direct orotracheal visualization without resting the device on the subject's tongue and that, during a bronchoscopic intubation, automatically ejects the endotracheal tube from the device as the endotracheal tube is advanced coaxially over a bronchoscope previous placed through the guide, thereby providing a mid-line entry of the bronchoscope and endotracheal tube, higher intubation success rate by lower skilled operators, and easy removal of the device from the patient's oral cavity.

10 Claims, 6 Drawing Sheets

RAPID OROTRACHEAL INTUBATION GUIDE

RELATED APPLICATION

This application claims the benefit of U.S. Provisional Patent Application No. 60/895,701, filed Mar. 19, 2007, the disclosures and drawings of which prior application are hereby incorporated by reference in their entirety.

BACKGROUND OF THE INVENTION

1. Field of the Invention

An orotracheal intubation guide simplifies the process of passing an endotracheal tube through a patient's mouth and larynx, and into the trachea. Orotracheal intubation is a common medical procedure that enables mechanically ventilated respiration, delivery of anesthesia to a patient's lungs, protecting patency of a patient's airway; an orotracheal guide can also be diagnostic visualizations such as bronchoscopy, operative procedures to the airway, and other diagnostic, surgical, and therapeutic procedures. When orotracheal intubation is performed improperly (e.g., producing an unrecognized esophageal intubation), the associated complications will rapidly lead to injury or death of the patient.

2. Description of the Related Art

Orotracheal intubation is commonly performed on an unconscious patient, or a patient under general anesthesia, using direct laryngoscopy, i.e., a laryngoscope is used to obtain a view of the glottis and an endotracheal tube is then inserted through the vocal cords under direct vision. Orotracheal intubation is commonly performed on a conscious patient using local anesthesia and direct laryngoscopy. Intubation of a conscious patient ensures ventilation and oxygenation even in the event of a failed intubation, and is preferred if difficulties are anticipated.

To minimize risks of injuring the vocal cords, of esophageal intubation, etc., various types of orotracheal intubation guides have been developed for use during intubation. Even under direct laryngoscopy, placement of a tube through the epiglottis and glottis is challenging, especially for those with little or infrequent intubation experience; "blind intubation" (not under direct vision) elevates risk of injury substantially. Airways compromised by collapse, tumors, folds, obesity, etc., also elevate risk of injury by intubation. Commonly available intubation guides, such as intubation stylets (e.g., U.S. Pat. No. 6,164,277 to Merideth, U.S. Pat. No. 5,773,241 to King, and U.S. Pat. No. 5,235,970 to Augustine), arcuate blades (e.g., U.S. Pat. No. 4,694,826 to Chester), spouts (e.g., U.S. Pat. Nos. 6,672,305 and 5,743,254 to Parker), and tubes (e.g., U.S. Pat. Nos. 5,203,320, 5,042,469, and 4,832,020 to Augustine) are not adjustable to a patient's specific oral conformation. "Oral conformation" means herein the three dimensional shape and structure of the upper respiratory tract excluding the nasal cavity; particularly the shape, structure, and relationship among the anterior maxillary arch, the hard and soft palate, pharynx, and larynx. Flexible bronchoscopes, laryngoscopes, and other endoscopes used for direct visualization of the orotracheal passage are herein individually called a "bronchoscope" and collectively called "bronchoscopes". Bronchoscopes can be navigated through body passages using means and methods known in the art. "Proximal" means at or in the direction of the exterior opening of a subject's mouth. "Distal" means in the direction of a subject's lungs through the passage comprising the oral cavity, pharynx, larynx, and trachea; this "oral tracheal" passage is called the "orotracheal passage". As used herein, "patient" and "subject" are synonymous.

Existing art devices (collectively including traditional airway devices and newer endoscopic airway devices) take the approach of giving the operator greater manipulative control over a bronchoscope, or combination of coaxial tube and bronchoscope, rather than orienting the guide based on the unique oral conformation of a given patient. Existing art devices often increase the level of skill required in orotracheal intubation, since the operator is manually and concurrently controlling at least an intubation tube and intubation guide, and often a bronchoscope, all of which are "floating untethered" within the oral cavity.

A recognized, but unsolved problem, in the intubation of conscious patients is avoiding a conscious patient's "gag reflex" during intubation. The "gag reflex" is triggered by pressure on the distal surface of the tongue; having to cope with a patient's gagging makes intubation much more difficult, especially when the operator must concurrently manipulate an endotracheal tube, a bronchoscope, and an intubation device. All known traditional airway devices, such as the Berman Intubating Pharyngeal Airway (Sun-Med, Inc., Largo Fla.), and all known endoscopic airway devices, such as the Ovassapian Fiberoptic Airway (Hudson RCI, Research Triangle Park, N.C.), contact and depress the distal surface of the tongue, which usually causes a gag reflex in a conscious patient. The gag reflex can be triggered not only upon intitial placement, but also during manipulation of the airway device to advance a bronchoscope down the airway. The gag reflex significantly, and undesirably, raises the risk factors in intubation of conscious patients, since the uncontrolled movement of the bronchoscope can damage a patient's vocal cords, cause the patient to bite the bronchoscope or endotracheal tube, or simply reduce the probability of successful intubation.

Existing art airway devices, since they rest on the tongue, can also easily deviate from the midline of the oral cavity, which deviation makes a midline approach to the vocal cords with a flexible bronchoscope more difficult. Existing art, devices are obtrusive, unstable, poorly tolerated in the awake patient, require a skilled operator, and necessarily increase the risk of injury to unconscious patients and to conscious patients.

There is demand for an intubation guide that adjusts to the specific oral conformation of a patient and does not require the operator to manually and concurrently control both the intubation tube and the intubation guide. The technical problem to be solved is to provide an intubation guide that adjusts to the oral conformation of a given patient and is removably affixed in a patient's oral cavity, and that does not rest on or otherwise rely on a patient's tongue for support, thereby allowing an operator to devote the operator's entire attention to advancing the endotracheal tube and/or bronchoscope down the orotracheal passage without manually holding a guide in position, and easily remove the guide when desired. A second technical problem to be solved is to provide a means of allowing a lower skilled operator, e.g., an operator who does infrequent intubations, a higher success rate of intubation without inducing a gag reflex in a patient and of maintaining a mid-line entry of the endotracheal tube and/or bronchoscope. The solution to these technical problems would require less skill to use, would not trigger the gag reflex in conscious patients, would consistently provide midline approaches to the vocal cords of a patient, and would be cost competitive with, and more accurate than, existing intubation guides.

SUMMARY OF THE INVENTION

The Rapid Orotracheal Intubation Guide ("ROTIG device") invention combines a bite tray for the maxillary arcade ("upper bite tray"), a bite tray for the mandibular arcade (lower bite tray, or lower bite trays, if fabricated as left lower bite tray and right lower bite tray), and a guide tube attached below the incisor area of the upper bite tray, which guide tube is split along the entire length of its lingual (inferior) aspect. The ROTIG device provides an orotracheal intubation guide that adjusts to the unique oral conformation of a given patient. A patient's dentition (or gingiva, as the case of edentulous subjects), when placed in the bite trays of a ROTIG device releasably secures the ROTIG device in the patient's oral cavity, orients the guide tube along the mid-sagittal plane of the oral cavity, and typically places the distal end of the guide tube just proximal to the palatine uvula. Placing the distal end of the guide tube just proximal to the palatine uvula and in the mid-sagittal plane is the optimal location for successful endotracheal intubation.

In a preferred intubation use, an operator selects a ROTIG device with a guide tube diameter such that coaxial advancement of an endotracheal tube over a previously inserted bronchoscope will cause the lingual aspect of the guide tube to splay open and release ("eject") the coaxial endotracheal tube and bronchoscope from the guide tube. The proximal opening of the guide tube is typically up to one (1) mm larger than the outside diameter of the endotracheal tube to be used; the preferred embodiment of the guide tube has a slight narrowing of the lumen in the distal direction. Generally speaking, the smallest inner diameter of the lumen of a guide tube is not smaller than the outside diameter of the endotracheal tube to be passed through the guide tube. Having selected the guide tube diameter, the operator inserts the ROTIG device in a patient's oral cavity, presses the superior dentition of the patient into the upper bite tray, and presses the inferior dentition of the patient into the lower bite tray. The operator slides an endotracheal tube coaxially up a bronchoscope (the bronchoscope is in the lumen of the endotracheal tube), leaving a distal length of the bronchoscope exposed, which distal length is at least equal to the intubation depth desired. The operator then inserts and advances the exposed distal end of the bronchoscope distally through the proximal opening of the guide tube of the ROTIG device and advances the bronchoscope. The operator navigates the bronchoscope down the orotracheal passage by direct visualization from the bronchoscope through the glottis and into the trachea, advancing the bronchoscope until the distal end of the bronchoscope is correctly placed ("operably positioned"). The operator then advances the coaxial endotracheal tube distally to contact the proximal opening of the guide tube, and then into the lumen of the guide tube. From the centrifugal expansion caused by the distal advance of the endotracheal tube, the lingual slit of the guide tube splays open and releases the endotracheal tube and bronchoscope from the guide tube by rupture of the slit in the lingual aspect of the guide tube. This release ("ejection") by the ROTIG device of the coaxial endotracheal tube and bronchoscope allows the operator to easily remove the ROTIG device from the patient's oral cavity. The ROTIG device is typically removed immediately after the endotracheal tube is operably positioned.

The guide tube can be constructed with a rapid or gradual narrowing of the lumen of the guide tube distal to the proximal opening of the guide tube; a rapid narrowing causes immediate ejection of the endotracheal tube (and bronchoscope in the lumen of the endotracheal tube) as the endotracheal tube is advanced through the proximal opening of the guide tube. Rapid ejection is preferred by some experienced operators. Since the distal end of the bronchoscope was previously placed at the distal position in the trachea desired by the operator (i.e., the distal tip was operably positioned), the endotracheal tube will follow the bronchoscope's path as the endotracheal tube is advanced distally; the operator stops advancing the endotracheal tube in the judgment of the operator, but typically when the endotracheal tube first becomes visible through the bronchoscope.

For use visualization uses with a bronchoscope (i.e., without intubation with an endotracheal tube), which visualization use is called "direct orotracheal visualization", an operator selects a guide tube distal opening diameter very slightly larger (e.g., approximately less than half a millimeter (<0.5 mm) than the outer diameter of the bronchoscope to be used. The guide tube for visualization uses typically has a constant diameter (non-narrowing) lumen, since ejection of the bronchoscope is typically not desired in visualization uses. The operator inserts the ROTIG device in the patient's oral cavity, has the patient bite the upper and lower bite trays, inserts the bronchoscope into the proximal opening of the guide tube, and advances and navigates the bronchoscope to the operable position desired, as described above, but without the use of an endotracheal tube. The operator typically leaves the ROTIG device in place in the patient's oral cavity until the visualization is completed; upon completion of the visualization, the bronchoscope is withdrawn and the ROTIG device then removed from the patient's oral cavity.

The ROTIG device enables fast and accurate intubation by guiding an endotracheal tube, which endotracheal tube is coaxially disposed around a bronchoscope, through the oral cavity so that the tube is correctly disposed to enter, successively, the pharynx, larynx, and trachea. In addition to facilitating procedures related to endotracheal tube intubation, such as induction anesthesia, uses of the ROTIG device include facilitation of direct transoral fiberoptic esophagoscopy ("direct esophagoscopy"), direct transoral fiberoptic bronchoscopy ("bronchoscopy"), and direct transoral fiberoptic laryngoscopy ("direct laryngoscopy").

Since the ROTIG device adjusts to the unique oral conformation of a given patient and is simple to use, it provides a much higher probability of successful intubation by a lower skilled operator. The "self-adjusting" path of the flexible guide tube is determined by the roof of a patient's oral cavity and distance between the patient's upper incisors and posterior pharyngeal wall. Importantly, the ROTIG device solves a technical problem of allowing a lower skilled operator, e.g., an operator who does infrequent intubations, a higher success rate of intubation without inducing a gag reflex in a patient and of maintaining a mid-line entry of the endotracheal tube and bronchoscope. The ROTIG device allows an operator to devote the operator's entire attention to advancing the bronchoscope or endotracheal tube down the orotracheal passage without manually holding a floating, untethered guide in position, especially a guide that rests on a patient's tongue. Since the ROTIG device does not rest on a patient's tongue, it is not destabilized by voluntary or involuntary movement of the tongue by the patient, does not trigger the gag reflex in conscious patients, and consistently provides midline approaches to the vocal cords of a patient. The ROTIG device is also cost competitive with existing intubation guides and can be packaged with intubation tubes. The ROTIG device is non-obtrusive and easily tolerated in an awake patient. So long as an awake patient in a sitting position has a functioning airway (a safe assumption), the ROTIG device is the only known intubation device that enables awake oral bronchoscopic intubation without intrusion of the intubation device distal to the distal oral cavity. The ROTIG device can be advantageously used for various procedures, including without limitation, direct esophagoscopy, direct bronchoscopy, direct laryngoscopy, and endotracheal tube intubation.

DETAILED DESCRIPTION OF THE PREFERRED EMBODIMENTS

A ROTIG device comprises the following structure: (a) an upper bite tray for a subject's upper (maxillary arch) teeth, which upper bite tray is joined or integral with, (b) a lower bite tray (which, in some embodiments, consists of a left lower bite tray and a right lower bite tray, each joined to the upper bite tray) for a subject's lower (mandibular arch) posterior teeth, and (c) a tube ("guide tube") attached to the lingual, proximal aspect of the upper bite tray, which guide tube has a proximal open end below the upper incisor area of the upper bite tray ("proximal opening" of the guide tube) and a distal open end projecting posterior to the molar area of the upper bite tray ("distal opening" of the guide tube), which guide tube is slit longitudinally along the entire length of the lingual aspect of the tube. The structural elements may be discrete and assembled into a ROTIG device, or they may be integral. The upper and lower bite trays are typically joined, or manufactured with an integral connecting section in the left and right molar areas of the upper and lower bite trays, which connecting section and associated areas of the ROTIG device function as a "bite block", as known in the dental arts.

To use a ROTIG device in a bronchoscopic intubation procedure, a physician or other health-care provider (collectively, "operator") places a ROTIG device in a subject's mouth, instructs a conscious subject to gently bite on the upper and lower bite trays (or in the case of an unconscious, unresponsive, uncooperative, or a veterinary (collectively, "unresponsive subject") subject, the operator manipulates the subject's mandible to cause the subject's maxillary and mandibular arcades to close within the upper and lower bite trays, respectively). The operator positions an endotracheal tube coaxially on the proximal end of a bronchoscope, as described above, and advances the exposed distal end of the bronchoscope distally through the proximal opening of the guide tube, through the guide tube to traverse the oral cavity and to emerge from the distal opening of the guide tube, and, thereafter, advances and navigates the bronchoscope distally to enter the pharynx in an optimum position to traverse the larynx and enter the trachea. When inserted and positioned for use in a subject's oral cavity, a ROTIG device does not press on the tongue and does not trigger a gag reflex. Moreover, movement of a subject's tongue is unencumbered, so that the operator can grasp a subject's tongue and pull it proximally to improve the visualization of the approach to the vocal cords. When the distal end of the bronchoscope is in the operable position in the judgment of the operator, the operator advances the endotracheal tube coaxially down the bronchoscope until the distal end of the endotracheal tube reaches the position desired by the operator. The slit in the lingual aspect of the guide tube facilitates ejection of the endotracheal tube from the ROTIG device when the tip of the endotracheal tube is advanced through the guide tube.

A ROTIG device is typically used to facilitate orotracheal intubation of a conscious subject, but can be used for unconscious subjects. Intubation using a ROTIG device is especially suitable for patients with unfavorable orotracheal anatomy, e.g., large tonsils, a low lying palate, obese, a large base of tongue, tumors of the oral cavity, pharynx, larynx, or trachea, or a patient with a cervical neurosurgical device which prevents extension or flexion of the neck. A ROTIG device is also used in patients who are generally at risk for tracheal intubation after induction anesthesia.

To use a ROTIG device, an operator typically administers topical or pharyngeal or orotracheal anesthesia for the patient's comfort prior to orotracheal bronchoscopic intubation. Such topical anesthesia is typically by one or more methods, e.g., (i) topical cetacaine spray and gargle, (ii) spraying both nasal airways with 4% xylocalne and 0.25% neosenephrine, (iii) tetracaine lollipops to the pharynx, (iv) nebulization of 2.5 cc of 4% xylocalne to the pharynx, larynx, and lungs, or (v) topical xylocalne piriform blocks with Jackson forceps.

The typical method of bronchoscope intubation using a ROTIG device is described above. In an alternative, less preferred, method of bronchoscope intubation using a ROTIG device with a larger distal opening, an operator slides the hub end of an endotracheal tube over the distal end of a bronchoscope and advances the endotracheal tube up the bronchoscope until the distal end of the endotracheal tube is aligned with (or slightly superior to) the distal end of the bronchoscope. The operator then advances the endotracheal tube and bronchoscope, coaxially disposed and with distal ends aligned (or approximately aligned), through the guide tube of a ROTIG device placed as described above in the patient's oral cavity, down the orotracheal passage, and places the distal ends of the bronchoscope and endotracheal tube in the trachea. This alternative method requires a guide tube diameter that does not automatically eject the coaxial endotracheal tube and bronchoscope; this method might be the used if the only available guide tube diameters are too large for use in the preferred method.

In both methods (bronchoscope advanced first, or bronchoscope and endotracheal tube advanced together), the bronchoscope is used to navigate the orotracheal passage, especially through a rima glottides, to avoid injury to plica vocalis and other tissue, and to select the depth of insertion of the endotracheal tube into the trachea. After placement of the distal end of the endotracheal tube in the trachea, the operator withdraws the bronchoscope through the proximal opening of the endotracheal tube, thereby removing the bronchoscope from the lumen of the endotracheal tube, which leaves the endotracheal tube in the orotracheal passage and the lumen of the endotracheal tube unobstructed. The appropriate location of the distal end of the endotracheal tube (operable position) is known in the art, but generally is sufficiently below the larynx to permit the cuff of the endotracheal tube to be properly inflated. The operator inflates the cuff of the endotracheal tube to prevent respiratory bypass of the endotracheal tube. A mechanical respirator is then connected to a fitting on the proximal end, or "hub", of the endotracheal tube.

The ROTIG device may be used with only a bronchoscope, without an endotracheal tube, e.g., for bronchoscopic inspection of orotracheal anatomy, which uses are called "bronchoscopic visualization" uses. For an awake patient in a sitting position (who invariably has a functioning airway), the ROTIG device is the only known device that provides a pathway for awake oral bronchoscopic intubation without the use of an oral airway device. Existing art airway devices are obtrusive and poorly tolerated in an awake patient.

Figure 1:
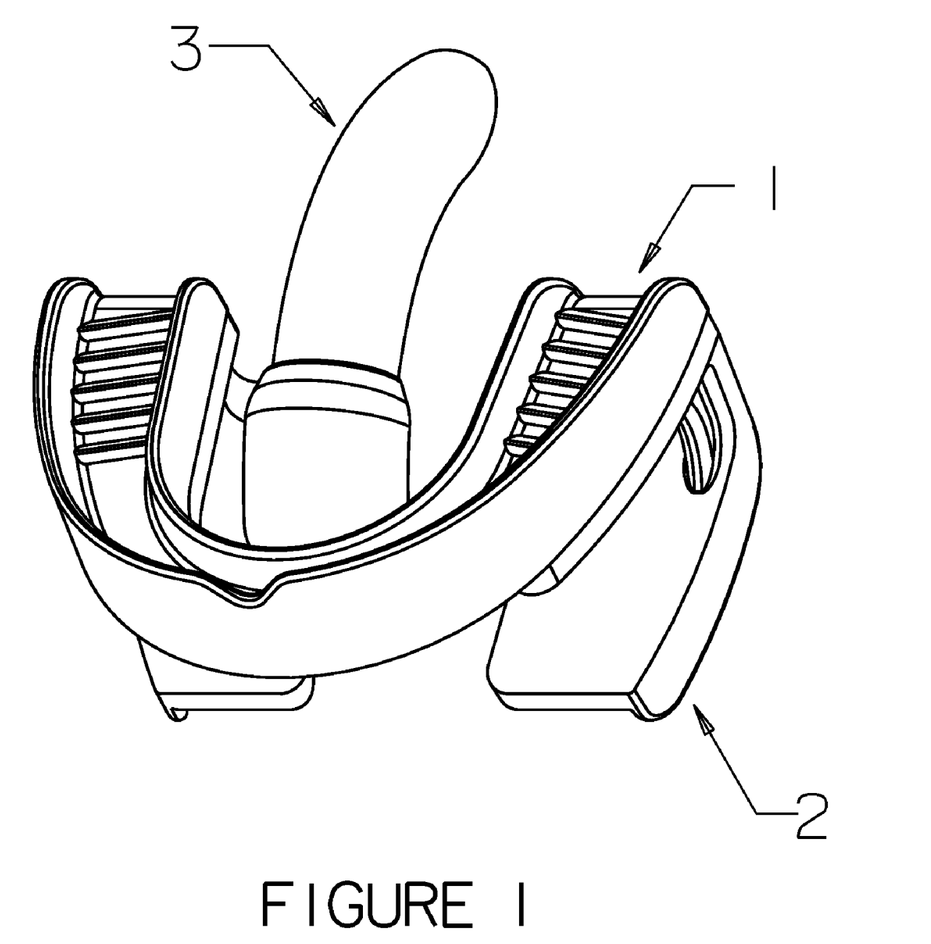
FIG. 1 shows a front perspective view of a ROTIG device.

FIG. 1 shows a front perspective view of a ROTIG device. The upper bite tray (1) is joined with a lower bite tray (2) and a guide tube (3). Upper bite tray (1), lower bite tray (2), and guide tube (3) can be fabricated as an integral unit, for instance, by injection molding, or as two pieces (e.g., bite trays as an integral piece and a separate guide tube that is affixed to the bite tray piece), or as three pieces (upper bite tray, lower bite tray, and guide tube) that are permanently or releasably attached to each other, or as four pieces (upper bite tray, left lower bite tray, right lower bite tray, and guide tube) that are permanently or releasably attached to each other, or as more than four pieces. For economics of production, the cost of injection molds and tooling is balanced against production volume; a single-piece injection mold for a single piece embodiment of the ROTIG device would typically be more expensive than molds for a two-piece, three-piece, or four-piece embodiments. Multiple piece embodiments of the ROTIG device permit different sizes of upper bite tray, lower bite tray, and guide tube to be combined. A two-piece embodiment (integral-bite-trays piece plus a guide tube piece that is combined with the integral-bite-trays piece to fabricate a complete ROTIG device) is the preferred embodiment, since a two-piece embodiment (i) permits different types and sizes of guide tube to be combined with different sizes and types of bite trays and (ii) reduces the total cost of molds and tooling, and complexity of injection molding, compared to a single-piece embodiment. In all embodiments, the lower bite tray (or left lower bite tray and right lower bite tray) does not extend proximally beyond the approximate area of the lower premolars, thereby permitting access to the proximal opening of the guide tube when the ROTIG device is placed in a patient's oral cavity.

Figure 2:
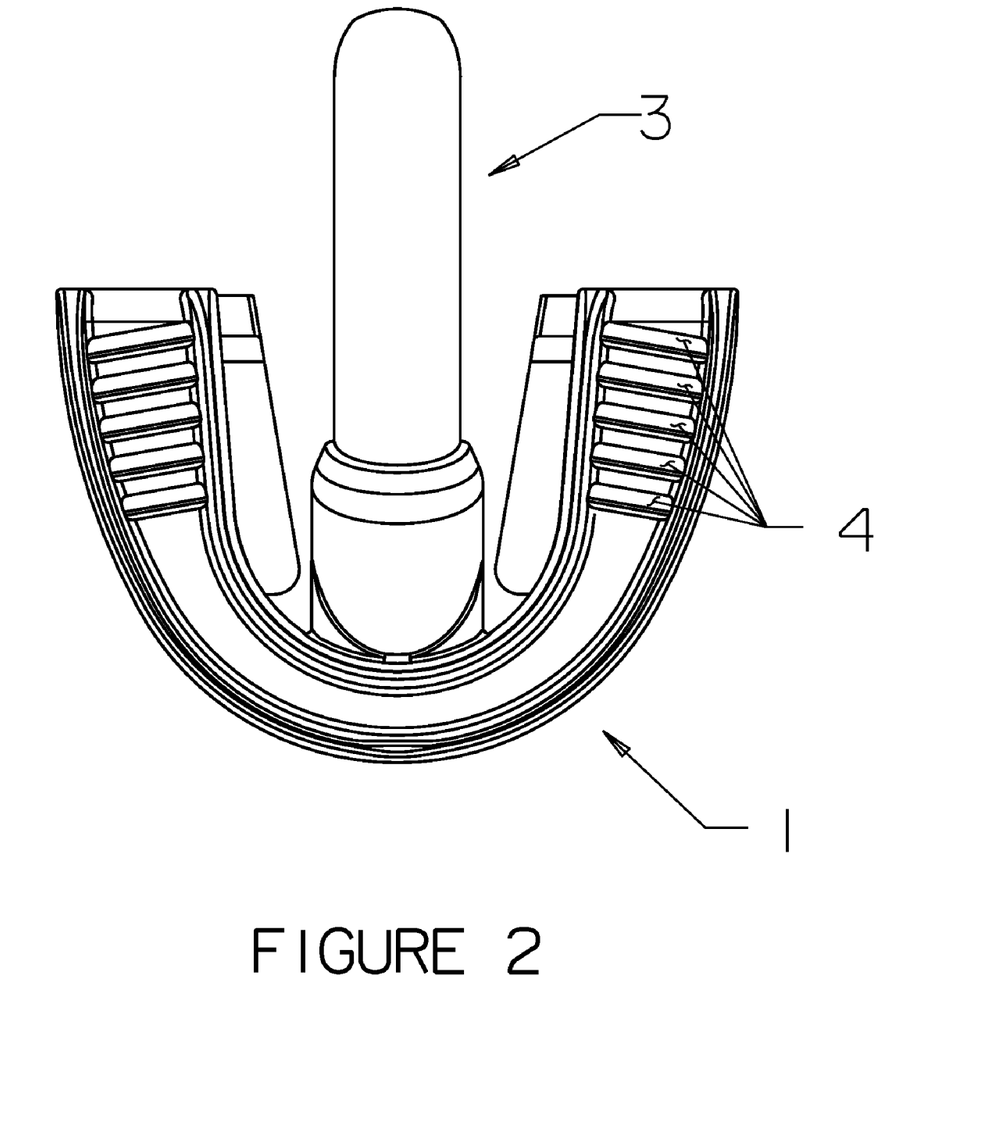
FIG. 2 shows a top view of a ROTIG device.

FIG. 2 shows a top view of a ROTIG device. The surface of the left and right molar areas of the upper bite tray contains serrations or teeth (4) that engage the upper dentition of a patient. The platform of the lower bite tray (not shown in FIG. 2) contains similar serrations or teeth.

Figure 3:
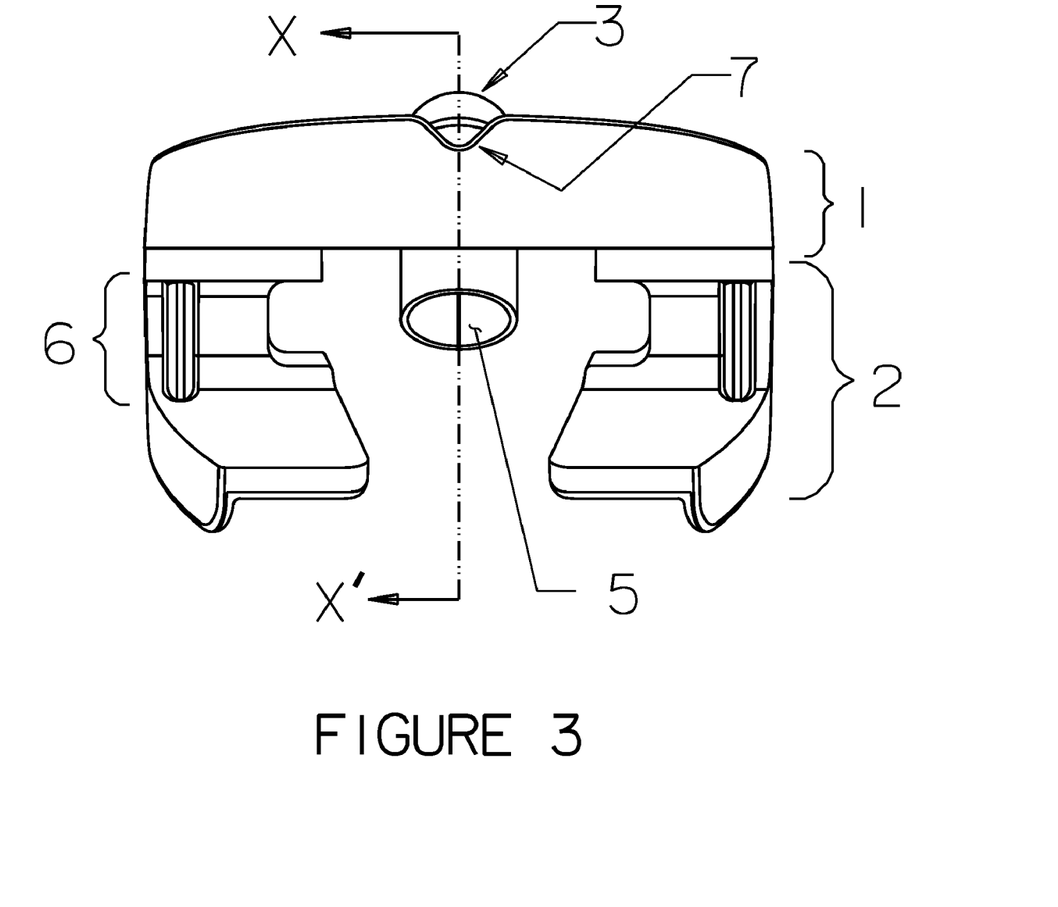
FIG. 3 shows a front view of a ROTIG device.

FIG. 3 shows a front view of a four-piece ROTIG device comprising upper bite tray, left lower bite tray (2), right lower bite tray, and guide tube (3). The upper bite tray (1) and the lower bite trays are sized for the oral cavity such that when a patient closes his mouth with a ROTIG device inserted in the patient's oral cavity, the upper dentition engages the upper bite tray, the posterior lower dentition engages the lower bite tray(s); the tongue has minimal, lateral contact with the lower bite tray(s) and no superior surface contact with the lower bite tray(s); and the guide tube (3) is stably positioned on the midline of the oral cavity. With the ROTIG device inserted in the patient's oral cavity, the proximal opening (5) of the guide tube is easily accessed through the patient's open mouth. The total height of the ROTIG device is determined by the joint height (6) in the junction of the upper and lower bite trays. The upper, proximal edge of the upper bite tray has a notch (7) to receive the patient's frenulum labii superioris; alternatively, the marginal flange of the entire upper bite tray can be shorter to avoid irritation of the frenulum labii superioris.

The flexibility of the guide tube accommodates variations in the distance from the incisors to the posterior pharyngeal wall by gently bending distally (downward) when the guide tube contacts the posterior pharyngeal wall. The distal tip of the guide tube is typically truncated to remove the somewhat sharp "feathered edge" that might otherwise irritate or lacerate the posterior pharyngeal wall. The flexibility of the guide tube also allows it to automatically conform to the contour of the hard and soft palate of the patient's oral cavity. These "self-adjusting" features of the ROTIG device are absent in prior devices.

Unlike prior art devices, these results are achieved without stimulating a gag reflex or relying on the tongue for stability of the intubation device. Also unlike prior art devices, the ROTIG device allows the operator to manipulate the tongue during the intubation procedure; manipulation of the tongue typically enables improved visualization of the vocal cords and ultimate success in advancing the bronchoscope past the vocal cords. Furthermore, unlike prior art devices, the ROTIG device protects a bronchoscope from inadvertent damage from the patient's biting down on the bronchoscope: the ROTIG device inherently functions as a bite block and protects the bronchoscope.

Figure 4:
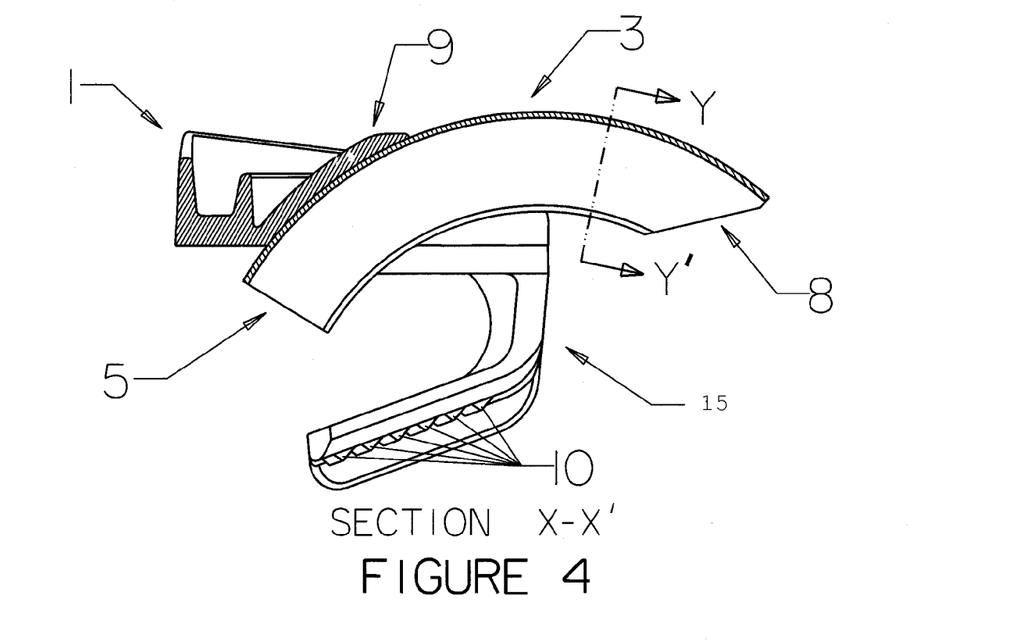
FIG. 4 shows a mid-sagittal cross-section of the ROTIG device of FIG. 3 along the X-X' axis.

FIG. 4 shows a mid-sagittal cross-section of the ROTIG device of FIG. 3 along the X-X' axis of FIG. 3. In this view, the full length of guide tube (3) is shown, with proximal opening (5) and distal opening (8) of the guide tube. An integral guide tube mounting bracket (9) is typically formed from the same material, and concurrently with, the upper bite tray (1). If the guide tube is fabricated as a separate piece from the upper bite tray, the guide tube (3) can be attached to the bracket (9) by adhesives, fusing, or other means of bonding plastic pieces known in the art. Optionally, bracket (9) can be fabricated to releasably engage guide tube (3) using a snap engagement, push-through engagement, or other type of deformation-based or friction-based engagement. The surface of the left and right molar areas of the left lower bite tray and right lower bite tray contains serrations or teeth that engage the lower dentition of a patient. In FIG. 4, the teeth (10) of the right lower bite tray (15) are visible.

Figure 5A:
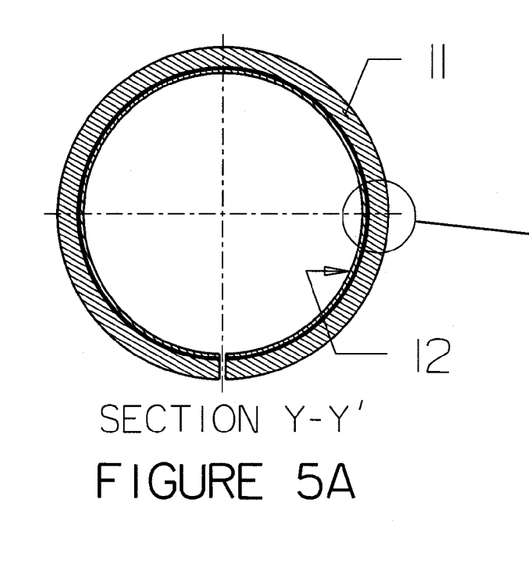
FIG. 5A shows a transverse cross-section view of the guide tube of a ROTIG device along the Y-Y' axis of FIG. 4.

FIG. 5A shows a transverse cross-section view of the guide tube of a ROTIG device along the Y-Y' axis of FIG. 4. The guide tube can be made of a uniform material (i.e., cylindrical, flexible tubular material), but is preferably fabricated with a somewhat flexible body material (11) and a lubricious lining (12). The lubricious lining (12) facilitates advancement of a bronchoscope and/or endotracheal tube.

Figure 5B:
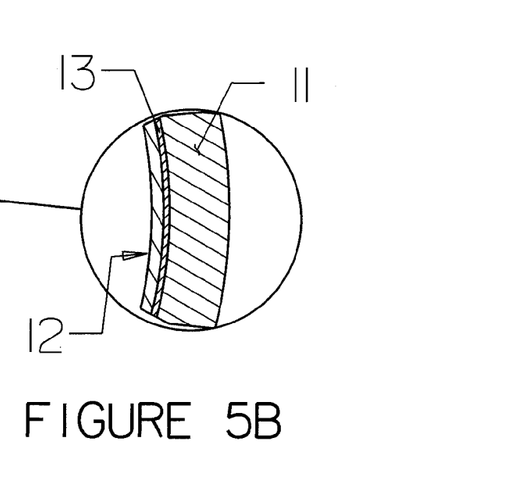
FIG. 5B shows a close-up of a portion of the annular wall of the guide tube of FIG. 5A.

FIG. 5B shows a close-up of a portion of a three-layer embodiment of the annular wall of the guide tube of FIG. 5A. The three-layer embodiment consists of a somewhat flexible body material (11), e.g., PVC with a Shore hardness of 80 A, a lubricious lining (12), e.g., polyethylene, and a middle layer (13), e.g., ethylene vinyl acetate, that binds well to the body material (11) and to the lubricious lining (12); such middle layer is used when the body material and lubricious lining do not bond well directly to each other.

Figure 6:
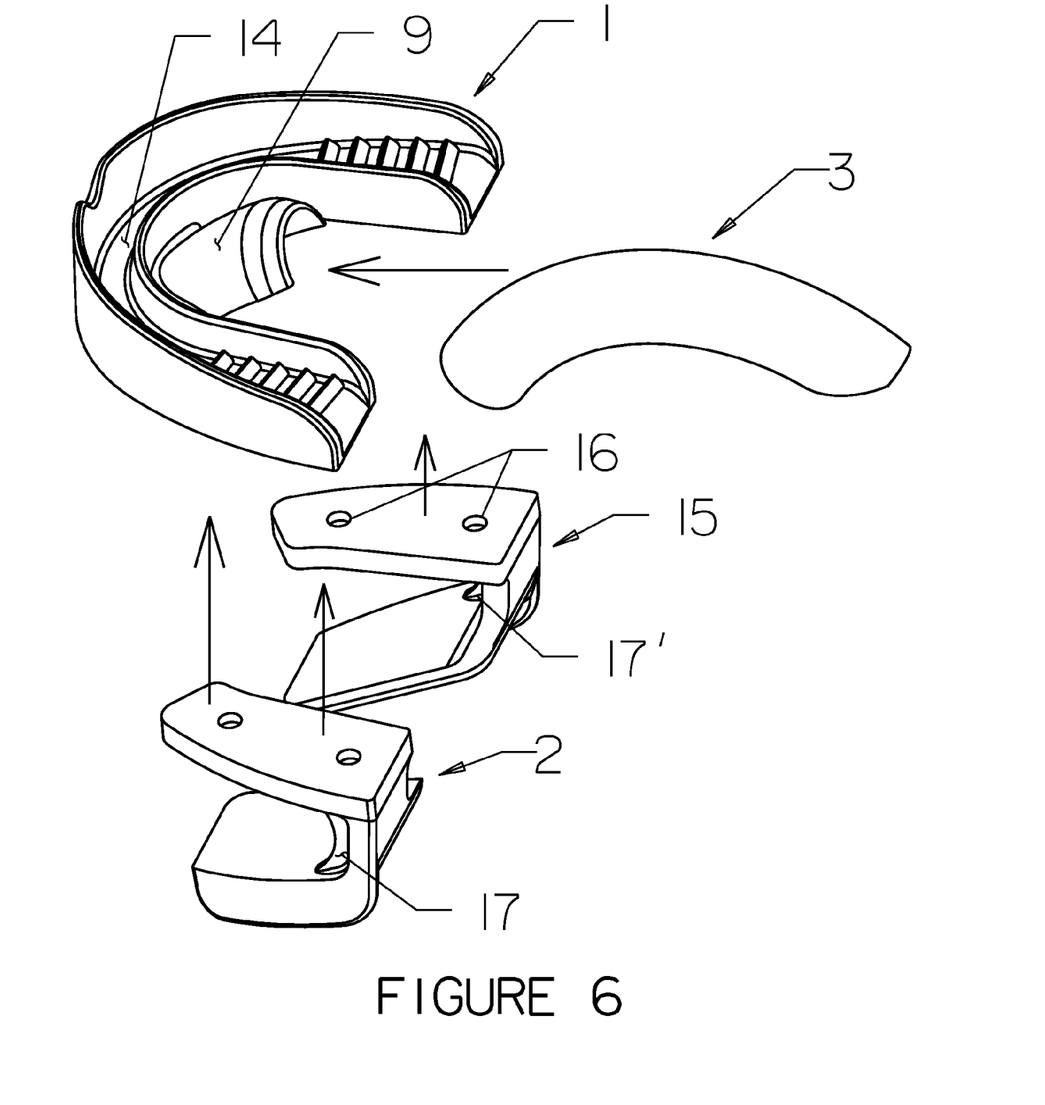
FIG. 6 shows an exploded view of a four-part embodiment of a ROTIG device.

FIG. 6 shows an exploded view of a four-piece embodiment of a ROTIG device. The arcade platform (14) of the upper bite tray (1) receives the upper dentition, and is narrower in the proximal region than in the molar (posterior) region. Left lower bite tray (2) and right lower bite tray (15) have optional alignment holes (with mating alignment pegs in the lower surface of the upper bite tray, which alignment pegs are not shown) to facilitate quick and correctly aligned assembly of the bite trays in a multi-piece embodiment. Alignment holes (16) are optional, and are obviated if the upper and lower bite trays are fabricated as a single piece. Reinforcement flanges (17, 17') are desirable, but are not required elements, that improve the resistance of the ROTIG device to compressive bite forces exerted by a patient. Mounting bracket (9) shown in FIG. 6 has an arc of approximately 180 degrees and is designed for affixing guide tube (3) using an adhesive or other bonding agent. An alternative mounting bracket designed to affix guide tube (3) in a snap (or pincer) fit would have an arc of substantially more than 180 degrees;

such snap fit would, however, make automatic ejection of an endotracheal tube and/or bronchoscope from the ROTIG device more difficult since the snap fit also increases the force necessary to splay open the lingual slit in the guide tube. The lingual slit of the guide tube is shown in FIG. 7.

Figure 7:
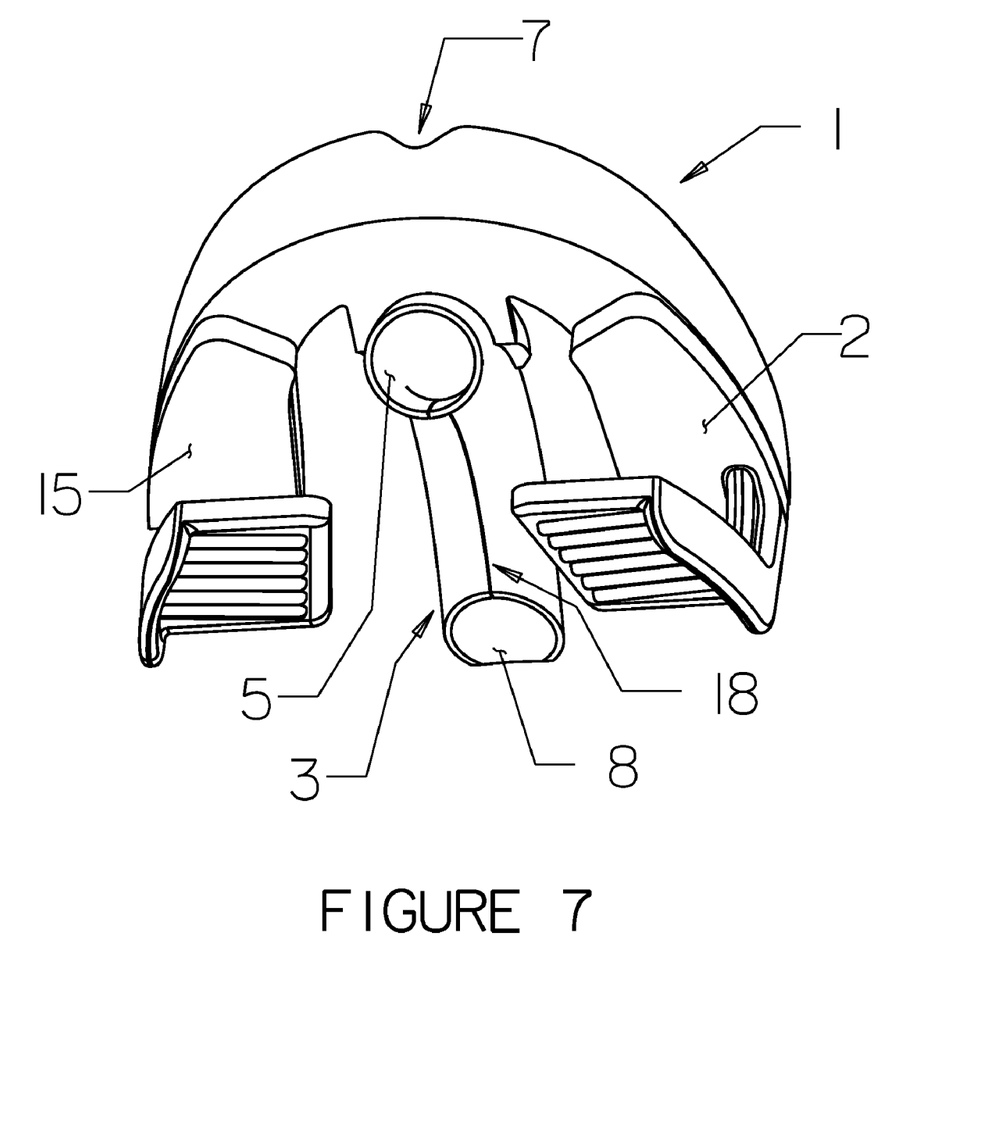
FIG. 7 shows a bottom perspective view of a ROTIG device.

FIG. 7 shows a bottom perspective view of a ROTIG device. Guide tube (3) is fabricated with a lingual slit (18) that connects the proximal opening (5) with the distal opening (8) of the guide tube. The lingual slit (18) is typically produced by cutting the full thickness of the annular wall of guide tube (3) during fabrication of the guide tube, typically as the tube is extruded. Guide tube is typically produced as a continuous spiral, then cut sectionally to the desired length. The lingual slit (18) can be cut as guide tube is extruded, while guide tube is in bulk, spiral form, or after guide tube sections have been cut to length. The lingual slit (18) in a ROTIG device allows ejection or removal of an endotracheal tube from the guide tube and subsequent removal the ROTIG device from a patient's oral cavity without disturbing an endotracheal tube and a bronchoscope that are being advanced, or have been advanced, to an operable position.

The upper bite tray of the ROTIG device is preferably made of a relatively soft plastic, e.g., polyvinyl chloride ("PVC") with a Shore hardness of 80 A. Such PVC is soft enough to provide cushioning for and conformance to the upper teeth or gums. The lower bite tray is a rigid material, preferably rigid PVC, because it must not collapse under bite pressure: the molar region of the lower bite tray functions as a bite block. PVC upper and lower bite trays can be easily glued together. PVC is a common material used in fabricated medical appliances, and PVC parts are easily bonded together with a variety of medically safe bonding agents.

The guide tube is preferably plasticized PVC of about Shore 80 A hardness, which is commonly used in flexible medical tubing. Plasticized PVC is a rather sticky, rubber-like material, however, so the lumen of the guide tube is typically coated or co-extruded with at least lubricious material to facilitate advancement of a bronchoscope. More lubricious materials, such as polyethylene ("PE"), are difficult to glue or bond to PVC. Therefore, the preferred construction of the guide tube, as shown in FIG. 5B, comprises a PVC Shore 80 A hardness PVC body (annular structural wall) material co-extruded with a middle, centripetal, "binding layer" of ethylene vinyl acetate ("EVA"), and an innermost, lubricious layer of PE. The PE (0.1 mm nominal thickness layer) binds well to EVA, and EVA binds well to PVC, which overcomes the poor binding of PE directly to PVC. This PVC to EVA to PE construction in medical tubing known in the medical industry, although such tubing is typically of a much smaller diameter and is used for drug infusion therapy. Based on the inventor's research, PVC to EVA to PE construction of a guide tube for an intubation device is novel. A lubricious innermost layer of the guide tube can also be created by electrodeposition of one or more lubricious agents, and by other means known in the art.

Alternate materials for the upper bite tray are thermoplastic elastomer (TPE) (of which there are several kinds known in the art), EVA, and thermoset rubbers, such as polyisoprene.

Immediately after placement of a ROTIG device in a patient's oral cavity, the operator typically confirms that the guide tube is aligned with the proximal to distal midline of the oral cavity by sighting down the longitudinal centerline of the guide tube and comparing that centerline with the centerline of the oral cavity. If visible, the uvula can be used a posterior reference point for the centerline of the oral cavity. If the guide tube is not aligned with the centerline of the oral cavity, the operator adjusts the alignment of the ROTIG device to obtain proper alignment.

A ROTIG device with an upper and lower bite tray(s), as described above, is the preferred means of providing a stable platform to anchor the guidance means in the ROTIG invention. In an alternative embodiment, the lower bite tray(s) can be omitted and a dental impression material is used in the arcade platform of an upper bite tray. The dental impression material releasably affixes the upper bite tray, with an attached means of guiding an endotracheal tube and/or a bronchoscope ("guidance means"), in the patient's oral cavity. If a "no lower bite tray" embodiment of the ROTIG device is used, the subject is asked to open his or her mouth and a bite block is placed in the subject's mouth; the bite block may be configured with a safety cord linking the bite block and the ROTIG device; the safety cord may be detachable from the ROTIG device. After placing the distal end of an endotracheal tube coaxially disposed with a bronchoscope in the trachea, the bronchoscope is removed, as described above. To remove a ROTIG device that lacks a lower bite tray (i.e., it has only an upper bite tray with attached guidance means), an operator wiggles the upper bite tray until the patient's upper dentition is freed from the dental registration material; the operator then pulls the ROTIG device free from the endotracheal tube and/or bronchoscope, and removes the ROTIG device from the patient's oral cavity. Various types of registration material known in the dental and mouth guard arts can be used.

A guide tube affixed to the upper bite tray, as described above, is the preferred guidance means in a ROTIG device. In an alternative embodiment, the guidance means can be replaced with a plurality of guide rings with a gap in the lingual aspect of each guide ring, which guide rings are attached in the palatal (superior) aspect of each guide ring to a palatal splint, which palatal splint is made of a malleable material and proximal end of which is affixed to the proximal area of the upper bite tray. The guide rings are affixed to the palatal splint by adhesives or other means known in the art. Guide rings can also be integral, e.g., created during the injection molding of the upper bite tray and palatal splint. The gap in the guide rings allows the ROTIG device to be removed from the endotracheal tube and/or bronchoscope, and from the patient's oral cavity, without disturbing the placement of the endotracheal tube. Palatal splints with guide rings can be made with one or more guide rings on a palatal splint, which palatal splint can be positioned or bent to provide a downward distal exit angle for a bronchoscope and/or endotracheal tube.

Bite trays can be made is different sizes, shapes, depths, and dentition coverage. If the subject's upper and/or lower dental arch is edentulous, bite tray(s) that engages the full, upper gingival and posterior lower gingiva are typically used; such bite trays may lack serrations or teeth (4, 10). ROTIG devices for pediatric use have smaller bite trays than those for adult use. The preferred width of an upper bite tray is typically tapered, wider in the molar area, narrower in the incisor area, as shown in FIG. 2. The preferred width of a lower bite tray is typically tapered, wider in the molar area, narrower in the premolar area, as shown in FIG. 7; lower bite trays typically do not extend into the canine and incisor areas and receive only the lower premolar and molar teeth (collectively, "lower posterior teeth").

The preferred mounting of a guide tube in embodiments of a ROTIG device for use in human subjects is to attach the guide tube to the proximal portion of the upper bite tray using a bracket made of the same material that is used to form the upper bite tray. In alternative embodiments, guide rings affixed to a palatal splint can be used instead of a guide tube;

for example, in veterinary uses, guide rings can be mounted on a strut, the height of a given strut is proportional to the distance of the hard palate above the tongue. Other shapes of tubular channels can be used, but circular channels are best adapted to the passage of bronchoscopes and endotracheal tubes through the lumen of a guidance means. Guide tubes and guide rings are herein collectively called "guides" and individually, a "guide". The diameter of the lumen of a guide is typically 5 to 12 mm, which accommodates standard bronchoscopes and endotracheal tubes. A guide lumen diameter of 3 to 4 mm is used for pediatric bronchoscopes and smaller endotracheal tubes, such as expandable endotracheal tubes. Guides with other lumen diameters can be made, e.g., for veterinary uses. A ROTIG device with a guide tube is the easiest to use, especially for novice operators, since the operator must navigate through the entrance of only one guide and the guide entrance is proximal and clearly visible.

A preferred guide embodiment (both tubes and rings) uses an annulus that is formed with a gap, e.g., by extrusion with a gap or by slitting a cylindrical tube. An alternative guide embodiment is formed with a longitudinal line of annular weakness in the inferior (lingual) aspect of the ring or tube (collectively, a "lingual break-away feature"). A breakaway feature ejects or releases a bronchoscope or endotracheal tube in the same way as a lingual slit.

A preferred embodiment of a guide has a conical, proximal face in which the annular wall is beveled around the exterior surface (outer diameter) of the guide and sloped inward to a recessed junction with the lumen of the guide ("funnel-face feature" or "infundibuliform"). This embodiment is best used with an endotracheal tube with a distal end annular face that is beveled from a protruding portion around the lumen (inner diameter) of the tube and sloped back to the exterior surface of the tube. Advancing the endotracheal tube distally against such a guide causes the beveled surfaces to slide against one another for easy advancement into the guide. The funnel-face feature is used in preferred embodiments of a ROTIG device. In addition to having a funnel-face feature, a guide tube can be made in a great variety of funnel shapes, e.g., sharply tapered proximal opening but with uniform diameter on the posterior (distal) portion of tubular guide, gradually tapered over the entire length of a tubular guide, etc.

A ROTIG device can be fabricated in several ways and using a variety of materials. The variously fabricated embodiments are distinguished by cost of production, by flexibility of use, and by tailoring to a specific type of subject. The lowest cost embodiment is a single elastomer ROTIG device in which the strength of a given portion of the ROTIG device is proportion to thickness of material and internal bracing, and in which all elements of the ROTIG device (bite trays, palatal splint (if any), and guide) are of the same material. Typically, the length and shape of a single elastomer ROTIG device are fixed. A single elastomer ROTIG device is typically manufactured using injection molding using, e.g., an ethylene vinyl acetate or plasticized polyvinyl chloride elastomer, and in various sizes to accommodate different bite trays and different oral conformations.

A slightly more costly, but far more flexible, embodiment of the invention is a two elastomer ROTIG embodiment in which the bite trays (and the core of the palatal splint, if any) are made of a less malleable, more resilient, elastomer, and the remainder of the ROTIG device (i.e., the guide tube, or the guide rings and layer surrounding the palatal splint in a palatal splint embodiment) is made of a more malleable, softer elastomer. Both elastomers could have an ethylene vinyl acetate backbone, but have different side groups that provide the desired resilience and malleability. A bite tray is typically made only of the less malleable, more resilient material and is not adversely distended by the forces of biting. A two elastomer ROTIG device is typically manufactured using injection molding.

An even more costly embodiment of the ROTIG device is made by using aluminum or other lightweight, malleable metal (collectively, "aluminum") as the core, and surrounding the aluminum core with a soft elastomer or other coating. An aluminum core ROTIG device can be manufactured using injection molding around the metal parts or by coating the aluminum parts after assembly with an elastomer. So long as the functional characteristics described above are provided, ROTIG devices can be manufactured using combinations of more than two elastomers or materials with the properties of elastomers, and such embodiments can contain metal or be free of metal.

A guide tube can be made in a length appropriate for use in the oral cavities of the largest subjects and the distal end of the guide trimmed for use in smaller oral cavities. An operator typically obtains or estimates the dimensions of a subject's oral cavity, and manipulates and/or trims the guide of the ROTIG device as necessary to fit a subject's oral cavity. A guide tube can be made with various degrees of malleability by the addition of a skeleton or spine, by use of copolymers, and by other means known in the art to add malleability or shape memory to flexible tubing. A malleable guide tube can be advantageously used to accommodate unusual anatomic features in a patient's oral cavity.

A ROTIG device could be made completely or partially of coated metal, ceramic, or natural product (wood, grass, collagen, etc.) materials, where the preferred coating is an elastomer that is comfortable to the subject. The surfaces of a ROTIG device that come into contact with the surfaces of a patient's oral cavity are typically made of a soft elastomer that is comfortable to the subject.

ROTIG devices can be fabricated as modules and assembled, rather than fabricated as an integral unit. The basic modular embodiment of a ROTIG device is an upper bite tray, a guide tube that is releasably or permanently affixed to the bracket on the upper bite tray, and lower bite tray(s) that is releasably or permanently affixed to the upper bite tray. An operator typically assembles a modular ROTIG device after measuring or estimating the dimensions of a subject's oral cavity and bite. Whereas integrally manufactured ROTIG devices may be stocked in a great number of variations of bite tray size and guide lengths to permit selection of an appropriately sized device, modular embodiments of the ROTIG device permit the operator to select specific bite tray width and depth, and a specific length and construction of a guide, and to assemble the selected modules into a ROTIG device. Modular embodiments of ROTIG devices may reduce stocking costs. The bite trays and guides of modular embodiments of ROTIG devices are fabricated using the same materials and methods as described above for integrally manufactured ROTIG devices, only they are fabricated as modules that can be snapped or glued together. The various methods known in the art of coupling elastomeric parts can be used to affix the modular pieces to assemble a ROTIG device, e.g., mechanical, adhesives, etc.

The preferred embodiment of a modular ROTIG device uses a close tolerance mechanical fitment and adhesive(s) to correctly align and stably join the bite trays and guide. ROTIG devices are intended to be disposed of after use with a single subject. However, a modular ROTIG device assembled without adhesives (snap fit) or with releasable adhesives can be disassembled after use, and sterilized for later reuse; any parts containing dental registration material are discarded. Fully modular ROTIG devices are typically used in veterinary uses to accommodate an increased variety of oral cavity sizes and shapes.

While the invention has been described with reference to specific embodiments thereof, it will be understood that numerous variations, modifications and additional embodiments are possible, and all such variations, modifications, and embodiments are to be regarded as being within the spirit and scope of the invention.

I claim:

1. A device to facilitate orotracheal intubation or direct orotracheal visualization comprising an upper bite tray for a subject's upper teeth, a lower bite tray for the subject's lower posterior teeth wherein the lower bite tray is joined posteriorly with the upper bite tray, and a guide attached to a lingual aspect of the upper bite tray and disposed alone the mid-line of the device, wherein the guide does not rest on the subject's tongue and wherein the guide has a lingual slit or a lingual breakaway feature.

2. A device to facilitate orotracheal intubation or direct orotracheal visualization comprising an upper bite tray for a subject's upper teeth, a lower bite tray for the subject's lower posterior teeth wherein the lower bite tray is joined posteriorly with the upper bite tray, and a guide attached to a lingual aspect of the upper bite tray and disposed alone the mid-saggittal plane of the oral cavity, wherein the device does not rest on the subject's tongue and wherein the guide has a lingual slit or a breakaway feature.

3. A device to facilitate orotracheal intubation or direct orotracheal visualization comprising an upper bite tray for a subject's upper teeth, a lower bite tray for the subject's lower posterior teeth wherein the lower bite tray is joined posteriorly with the upper bite tray, and a guide attached to a lingual aspect of the upper bite tray and disposed alone the mid-line of the device, wherein the device does not rest on the subject's tongue, wherein the guide has a lingual slit or a breakaway feature, and wherein the guide ejects an endotracheal tube coaxially advanced over a bronchoscope as the endotracheal tube is advanced through the guide.

4. The device of claims 1, 2, or 3, wherein the construction of the device is selected from the group comprising: integral upper and lower bite trays and guide; integral upper and lower bite trays and separate guide that is affixed to the upper bite tray; upper bite tray, lower bite tray that is affixed to the upper bite tray, and guide that is affixed to the upper bite tray; upper bite tray, left lower bite tray that is affixed to the upper bite tray, right lower bite tray that is affixed to the upper bite tray, and guide that is affixed to the upper bite tray.

5. The device of claims 1, 2, or 3, wherein the guide of the device is a guide with a construction selected from the group comprising: cylindrical, flexible guide tube of uniform material; guide with plastic annular wall and lubricious lining of the lumen of the guide; and guide with plastic annular wall, lubricious lining of the lumen of the guide, and a layer intermediate between the annular wall and lubricious lining.

6. The device of claims 1, 2, or 3, wherein the bite trays of the device are constructed of material selected from the group comprising polyvinyl chloride, plasticized polyvinyl chloride, ethylene vinyl acetate, thermoplastic elastomer, and thermoset rubber.

7. The device of claims 1, 2, or 3, wherein the upper bite tray has a proximal notch to accommodate the frenulum labii superioris.

8. The device of claims 1, 2, or 3, wherein the guide of the device is a guide constructed with flexible plastic material such that contact by the distal tip of the guide with the posterior pharyngeal wall causes the guide to bend distally.

9. The device of claims 1, 2, or 3, wherein the subject's tongue can be freely manipulated with the device in place in the subject's oral cavity.

10. The device of claims 1, 2, or 3, used for a procedure selected from the group comprising direct esophagoscopy, direct bronchoscopy, direct laryngoscopy, and endotracheal tube intubation.

* * * * *